US010945666B2

(12) United States Patent
Karst et al.

(10) Patent No.: US 10,945,666 B2
(45) Date of Patent: Mar. 16, 2021

(54) SKIN DEVICE INCLUDING A FLEXIBLE AREA AND MEANS FOR LIMITING BENDING

(71) Applicant: COMMISSARIAT A L'ENERGIE ATOMIQUE ET AUX ENERGIES ALTERNATIVES, Paris (FR)

(72) Inventors: Nicolas Karst, Folkling (FR); Fabrice Emieux, Voreppe (FR); Simon Perraud, Bandol (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/311,121

(22) PCT Filed: May 11, 2015

(86) PCT No.: PCT/IB2015/053456
§ 371 (c)(1),
(2) Date: Nov. 14, 2016

(87) PCT Pub. No.: WO2015/177676
PCT Pub. Date: Nov. 26, 2015

(65) Prior Publication Data
US 2017/0079584 A1 Mar. 23, 2017

(30) Foreign Application Priority Data
May 19, 2014 (FR) ...................................... 14 54461

(51) Int. Cl.
*A61B 5/00* (2006.01)
*A61N 1/04* (2006.01)
(Continued)

(52) U.S. Cl.
CPC ............ *A61B 5/683* (2013.01); *A61B 5/0402* (2013.01); *A61F 13/00021* (2013.01);
(Continued)

(58) Field of Classification Search
CPC ... A61B 5/0205; A61B 5/6831; A61B 5/6804; A61B 2560/0412; A61B 5/02438; A61B 5/04
(Continued)

(56) References Cited

U.S. PATENT DOCUMENTS 3,472,233 A 10/1969 Sarbacher
3,525,330 A * 8/1970 Greene ................ A61B 5/6805
600/382
(Continued)

OTHER PUBLICATIONS

International Search Report dated Aug. 31, 2015, issued in corresponding International Application No. PCT/IB2015/053456, filed May 11, 2015, 8 pages.
(Continued)

*Primary Examiner* — Joseph A Stoklosa
*Assistant Examiner* — Brian M Antiskay
(74) *Attorney, Agent, or Firm* — Christensen O'Connor Johnson Kindness PLLC (57) ABSTRACT

The invention relates to a device intended for being attached to the skin of a user, the device being substantially planar and including at least one flexible area in which the device can be bent relative to an axis located in the plane of the device, and in which components sensitive to bending are placed, the device including means for limiting the bending such as to limit the bending of said at least one flexible area of the device relative to at least one axis located in the plane of the device.

27 Claims, 11 Drawing Sheets

(51) Int. Cl.
*A61F 13/00* (2006.01)
*A61B 5/0402* (2006.01)

(52) U.S. Cl.
CPC ...... *A61F 13/00038* (2013.01); *A61N 1/0456* (2013.01); *A61N 1/0472* (2013.01)

(58) Field of Classification Search
USPC ................ 600/300, 372, 382–393, 508–509
See application file for complete search history.

(56) References Cited

U.S. PATENT DOCUMENTS

| | | | | |
|---|---|---|---|---|
| 4,202,344 A * | 5/1980 | Mills | ................ | A61B 5/04085 600/382 |
| 5,329,923 A * | 7/1994 | Lundquist | .......... | A61B 18/1492 600/373 |
| 5,435,313 A * | 7/1995 | Noda | .................... | B06B 1/0622 600/459 |
| 6,374,143 B1 * | 4/2002 | Berrang | ............... | A61N 1/0541 600/379 |
| 6,725,090 B1 | 4/2004 | Lattin et al. | | |
| 8,666,471 B2 * | 3/2014 | Rogers | ..................... | A61B 5/05 600/373 |
| 9,468,384 B2 * | 10/2016 | Kolberg | ............... | A61B 5/6846 |
| 2003/0092978 A1 * | 5/2003 | Fisher, III | ............ | A61B 5/0408 600/391 |
| 2010/0280573 A1 | 11/2010 | Schouenborg | | |
| 2012/0206248 A1 * | 8/2012 | Biggs | ................. | H01L 41/0833 340/407.2 |
| 2012/0226130 A1 * | 9/2012 | De Graff | .................. | A61B 1/05 600/393 |
| 2012/0310070 A1 * | 12/2012 | Kumar | ................ | A61B 5/6833 600/391 |
| 2013/0313713 A1 | 11/2013 | Arora et al. | | |
| 2014/0240108 A1 * | 8/2014 | Matthews | ............... | G08B 6/00 340/407.1 |
| 2015/0065840 A1 * | 3/2015 | Bailey | .................. | A61B 5/6802 600/384 |
| 2015/0094558 A1 * | 4/2015 | Russell | .................. | A61B 5/688 600/391 |
| 2015/0265173 A1 * | 9/2015 | Datovech | ........... | A61B 5/04085 600/393 |
| 2016/0195902 A1 * | 7/2016 | Huh | ........................ | G06F 3/017 345/156 |

OTHER PUBLICATIONS

Rapport de Recherche Préliminaire dated Sep. 10, 2014, issued in priority French Application No. 1454461, filed May 19, 2014, 1 page.
Written Opinion dated Aug. 31, 2015, issued in corresponding International Application No. PCT/IB2015/053456, filed May 11, 2015, 6 pages.
Written Opinion of the International Searching Authority dated Aug. 31, 2015, issued in corresponding International Application No. PCT/IB2015/053456, filed May 11, 2015, 12 pages.
International Preliminary Report on Patentability dated Nov. 22, 2016, issued in corresponding International Application No. PCT/IB2015/053456, filed May 11, 2015, 1 page.

\* cited by examiner

SKIN DEVICE INCLUDING A FLEXIBLE AREA AND MEANS FOR LIMITING BENDING

The invention relates to the technical field of devices intended to be fixed on the skin of a user.

In particular relates to medical devices, such as cutaneous electrodes for measuring physiological parameters or for electro stimulation, or pulse generators for electric stimulation.

Indeed, in order to be able to check a certain number of physiological parameters in real-time, physicians increasingly use portable medical devices so that the patient is not forced to remain in a medical structure during the monitoring period. In addition to increased patient comfort, this makes it possible to decrease the costs related to the use of these medicalized structures and also, over time, to effectively accompany patients on a daily basis as they deal with their diseases.

In order to further improve the comfort and ergonomics of these medical devices, devices have been proposed in the form of patches are generally energy-autonomous and intended to be worn directly on the patient's skin. We may in particular site the use of patches making it possible to perform electrocardiograms or to generate electric pulses for electro stimulation of the nerves used to treat pain.

In order to be as ergonomic as possible and must comply with the different parts of the human body on which it may be positioned, the device must be as thin and flexible as possible.

However, it is also necessary to protect the elements of the device that may be damaged by repeated flexure, such as electronic components, the batteries, the printed circuit for the metal tracks. That is why these elements are generally positioned in rigid structures and only the electrodes are flexible.

Thus, the device described in document US 2013/0096641 is made up of rigid unit integrating the electronics in the power source making a possible to deliver electric pulses and that is mounted on an adhesive patch making it possible to keep the unit in contact with the skin.

Likewise, in the device described in document WO 2013/106644, the flexure-sensitive elements are protected in a rigid unit, only the parts serving as electrodes being flexible.

In these devices, the presence of a rigid unit makes it possible to effectively protect the flexure-sensitive elements, but greatly limits the comfort and ergonomics of the devices.

The invention aims to offset these drawbacks by proposing a device intended to be fixed on the skin of a user that is simultaneously thin, flexible and robust, while providing protection for the components of the device that may be damaged in particular by the stresses generated by the flexure of the device.

Thus, the invention relates to a device intended to be fixed on the skin of a user, the device being substantially planar and comprising at least one flexible zone in which the device can be bent relative to an axis situated in the plane of the device and in which flexure-sensitive components are situated, the device comprising means for limiting the flexure to limit the flexure of said at least one flexible zone of the device relative to at least one axis situated in the plane of the device.

In a first embodiment, said means comprises an elongated central part, on either side of which protruding parts extend that define recesses between them.

The flexure limiting means define a determined curve radius at a flexure zone. The minimum value of the curve radius depends on the width L corresponding to the space between the two protruding parts and the height H of the protruding parts.

In order to obtain that this curve radius limiting effect, L and H should be chosen such that $L < \pi H$, and preferably, $L < 2H$.

In a first alternative embodiment, said means are situated in a substantially central part of the device.

In a second alternative embodiment, said means are situated along at least part of the periphery of the device.

In a third alternative embodiment, said means include a part situated at the periphery of the device and a part extending substantially at the center of the device.

Advantageously, the surface occupied by said means is less than 50% of the surface of the device, and preferably less than 10% of the surface.

In a second embodiment of the device, the means for limiting the flexure are formed by the encapsulating unit of the device.

Preferably, the device advantageously comprises at least two rigid parts connected by a flexible zone, in which flexure-sensitive components are situated, each of said rigid parts comprising at least two walls of the encapsulating unit, the walls opposite two adjacent rigid parts constituting means for limiting the flexure along an axis extending in said flexible zone and parallel to said walls.

Advantageously, the height (H) of the walls and the width (L) of the spacing between two opposite walls are such that $L < \pi H$, and preferably, $L < 2H$.

In a first alternative embodiment, the device comprises a plurality of rigid parts connected to one another in pairs by a flexible zone and extending along a determined direction.

In a second alternative embodiment, at least four rigid zones are connected to one another by at least two flexible zones extending in two different directions.

The invention will be better understood and other aims, advantages and features thereof will appear more clearly upon reading the following description, done in reference to the appended drawings, in which.

The elements shared by the different figures will be illustrated by the same references.

Figure 1:
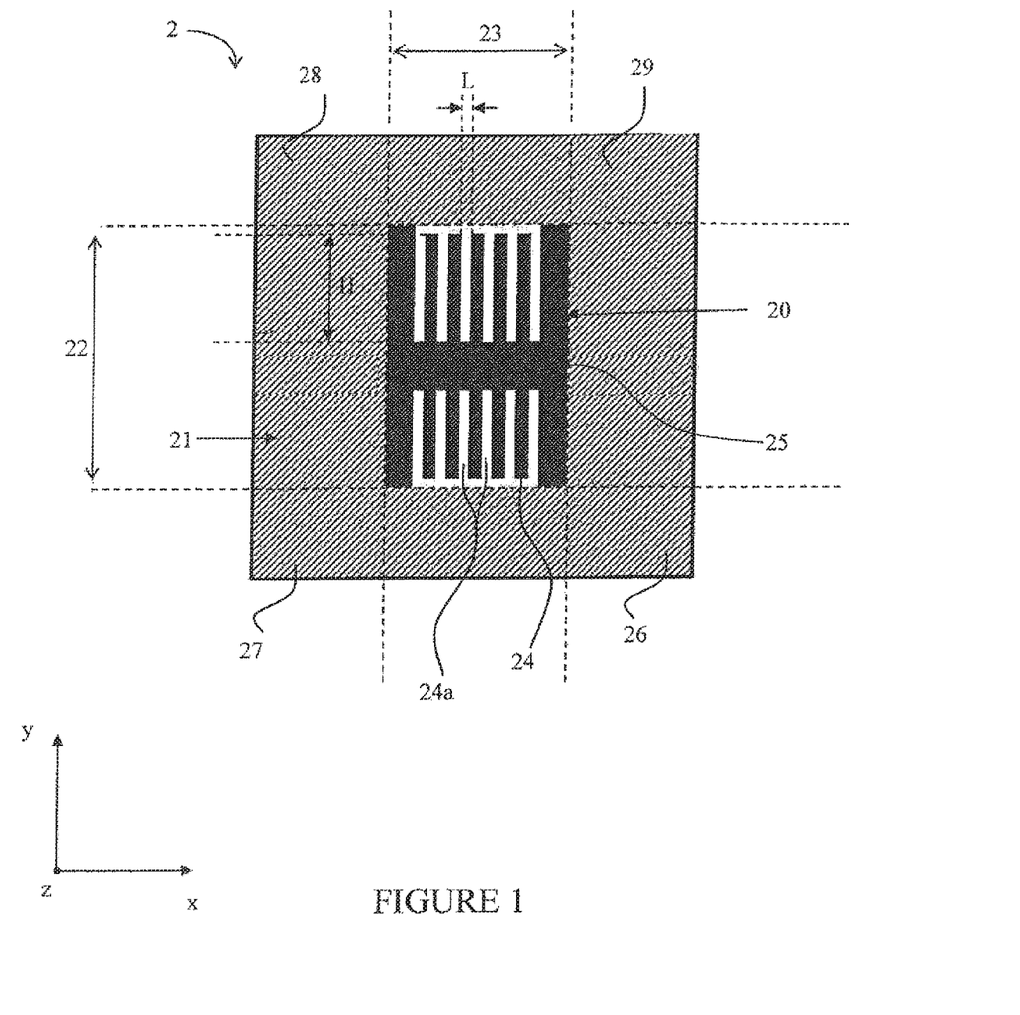
FIG. 1 is a top view of a first example embodiment of a device according to the invention, FIG. 2 comprises FIGS. 2A and 2B, which are perspective views of a flexible planar element in the absence and presence of flexure relative to the parallel axis x.

FIG. 1 shows a top view of a first example of the device according to the invention.

Figure 2A:
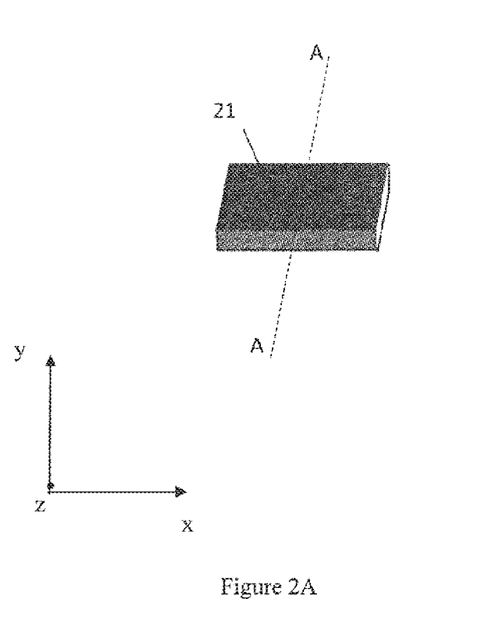
Figure 2B:
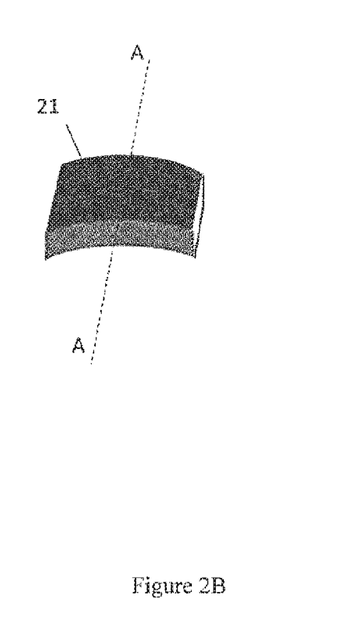

This device 2 comprises a planar element 21, here square, and contained in a plane xy also shown in FIG. 2. This element 21 includes flexure-sensitive elements.

The flexure-sensitive elements can in particular be electronic components, metal tracks, printed circuits or power sources.

The element 21 is hollowed out and receives, substantially centrally, a flexure limiting element 20. Said element 20 is able to limit the flexure of the device.

The element 21 makes it possible to define the zones 22 and 23 of the element 21, both situated in the extension of the element 20, along the axis x and along the axis y, in two opposite directions. The other zones of the element 21 are identified by references 26 to 28. They are situated in the corners of the element 21 and are defined by the dotted lines indicated in FIG. 1.

This flexure limiting element 20 includes an elongated central part 25, on either side of which protruding parts 24 extend defining recesses 24a. In the example illustrated in FIG. 1 and in top view, the protruding parts extend in the plane xy.

Of course, the element 20 has a certain thickness, like the element 21. They therefore also have a component along an axis z perpendicular to the plane xy, corresponding to the thickness. Thus, the central part extends along a plane xz.

Owing to its structure, the flexure limiting element 20 will completely prevent the flexure of the device 2 relative to any axis parallel to the axis x, at the zone 22.

FIG. 2 illustrates the effect of flexure around an axis AA parallel to the axis y on the element 21, which extends in the plane xy.

This flexure limiting element 20 will also make it possible to limit the flexure to a determined curve radius, at the zone 23, relative to any axis parallel to the axis y, and therefore to protect the flexure-sensitive elements, situated at the flexure zone 23, from excessive flexure relative to an axis parallel to the axis y, that could damage them.

The limitation of the curve radius is obtained by choosing the width L corresponding to the spacing between two protruding parts and the height H of these protruding parts appropriately.

Thus, L and H are chosen such that $L<\pi H$ and, preferably, $L<2H$.

However, in this configuration, the flexure sensitive elements may not be effectively protected from flexure relative to any axis parallel to the axis y at the zones 28 and 29, or the zone 23. Likewise, the flexure sensitive elements cannot be effectively protected from flexure along any axis parallel to the axis x at the zones 26 and 27.

Furthermore, to protect zones having a large surface, the flexure limiting element 20 illustrated in FIG. 2 must occupy an equally significant surface, which decreases the surface occupied by the different components of the device accordingly.

Figure 3:
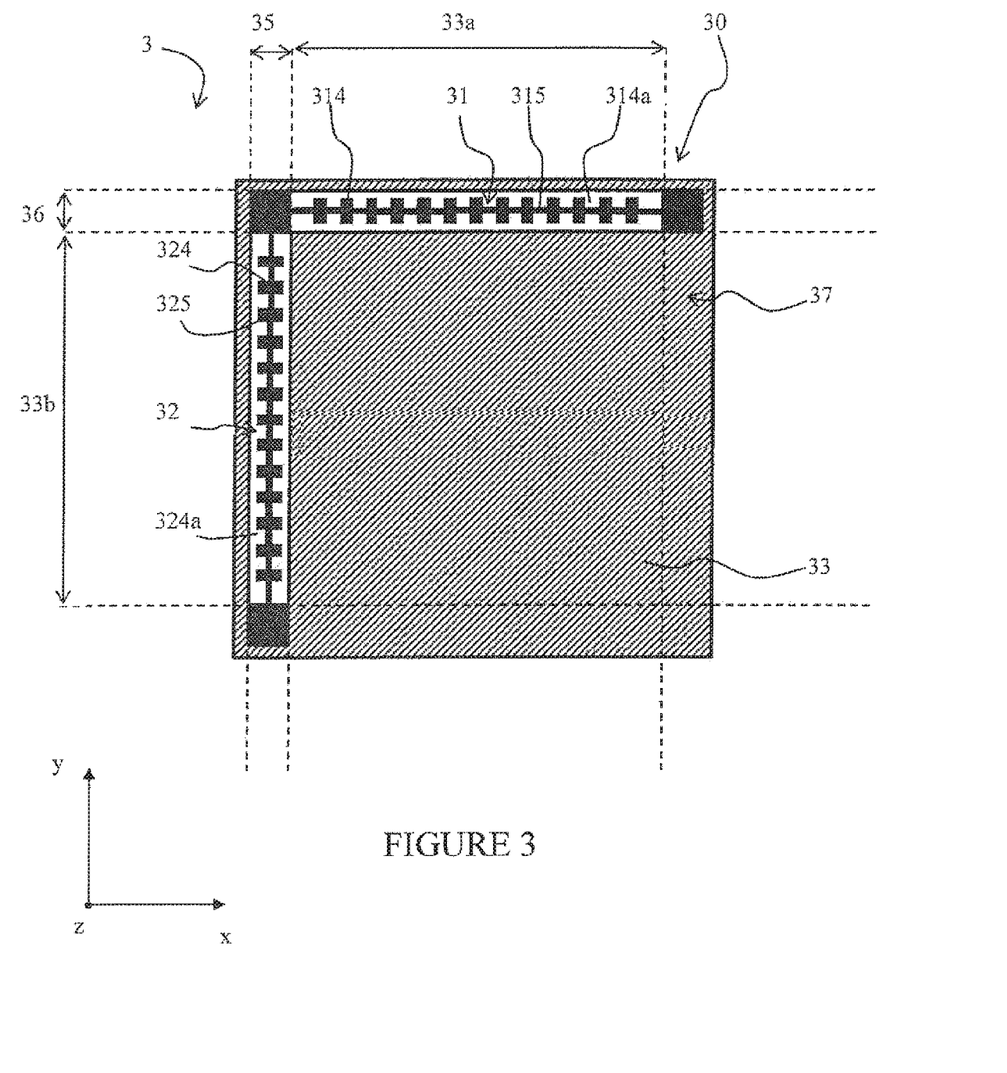
FIG. 3 is a top view of a third embodiment of a device according to the invention.

Reference is now made to FIG. 3, which illustrates, in top view, another embodiment of the device according to the invention making it possible to ensure better protection of the components of the device, against flexure, irrespective of the axis relative to which it occurs.

In this embodiment, the device 3 is again substantially planar and extends along the plane xy. It also has a certain thickness and therefore a component along the axis z perpendicular to the plane xy. It preferably has a square shape and includes flexure sensitive elements on its surface 37.

It includes an element 30 intended to limit the flexure.

In this example embodiment, this flexure limiting element 30 is made up of two parts 31 and 32 extending in different directions.

In the example illustrated in FIG. 3, these two parts 31 and 32 are perpendicular and extend along two adjacent sides of the device 3. Other configurations could be considered, like those described in reference to FIGS. 4 to 7.

Each part 31 and 32 of the flexure limiting element 30 has the same general structure as the flexure limiting element 20 illustrated in FIG. 1.

Thus, each of them includes an elongated central part 315, 325, on either side of which protruding parts 314, 324 extend, defining recesses 314a, 324a.

Owing to this particular structure, the element 30 makes it possible to limit the flexure of the device 3 over its entire surface 37, relative to any axis, parallel to the axis x or the axis y.

The element 30 defines a substantially square zone 33, the two sides of which are identified by references 33a and 33b, as well as two zones 35 and 36 corresponding to the part of the surface 37 occupied by the parts 32 and 31 of the element 30. The two sides 33a and 33b correspond to the length of the parts 31 and 32, which play an active role in limiting the flexure, i.e., the length of the central part.

The zones 35 and 36 are not intended to receive components, inasmuch as they are occupied by the element 30.

The part 31 of the element 30 makes it possible to limit the flexure of the device 3 to a determined curve radius at the zone 33, relative to any axis parallel to the axis y. The part 32 also makes it possible to limit the flexure of the device 3 to a determined curve radius at the zone 33 relative to any axis parallel to the axis x. To that end, it suffices for the height H and the spacing L of the protruding parts to be such that $L<\pi H$, and preferably, $L<2H$.

Lastly, the element 30 completely prevents flexure at the zone 35 relative to any axis parallel to the axis y, as well as the flexure at the zone 36, relative to any axis parallel to the axis x.

Advantageously, the surface occupied by the flexure limiting element 30 will be less than 50% of the total surface of the device 3, and preferably less than 10%.

With this flexure limiting element 30, the surface of the zones where the flexure is impossible is relatively limited and will be defined by the surface occupied by the element 30.

This is advantageous relative to the embodiment of FIG. 1. Indeed, the device is intended to be placed on a user's body. It is therefore advantageous to limit the surface occupied by the zones making flexure completely impossible as much as possible.

Thus, for a device measuring 5×5 cm$^2$, the surface occupied by the flexure limiting element 30 may be limited to 15% for parts 31 and 32 whereof the width is about 0.5 cm.

The minimum curve radius relative to any axis parallel to the axis x and relative to any axis parallel to the axis y will be less than 5 cm, preferably less than 2 cm.

Figure 4:
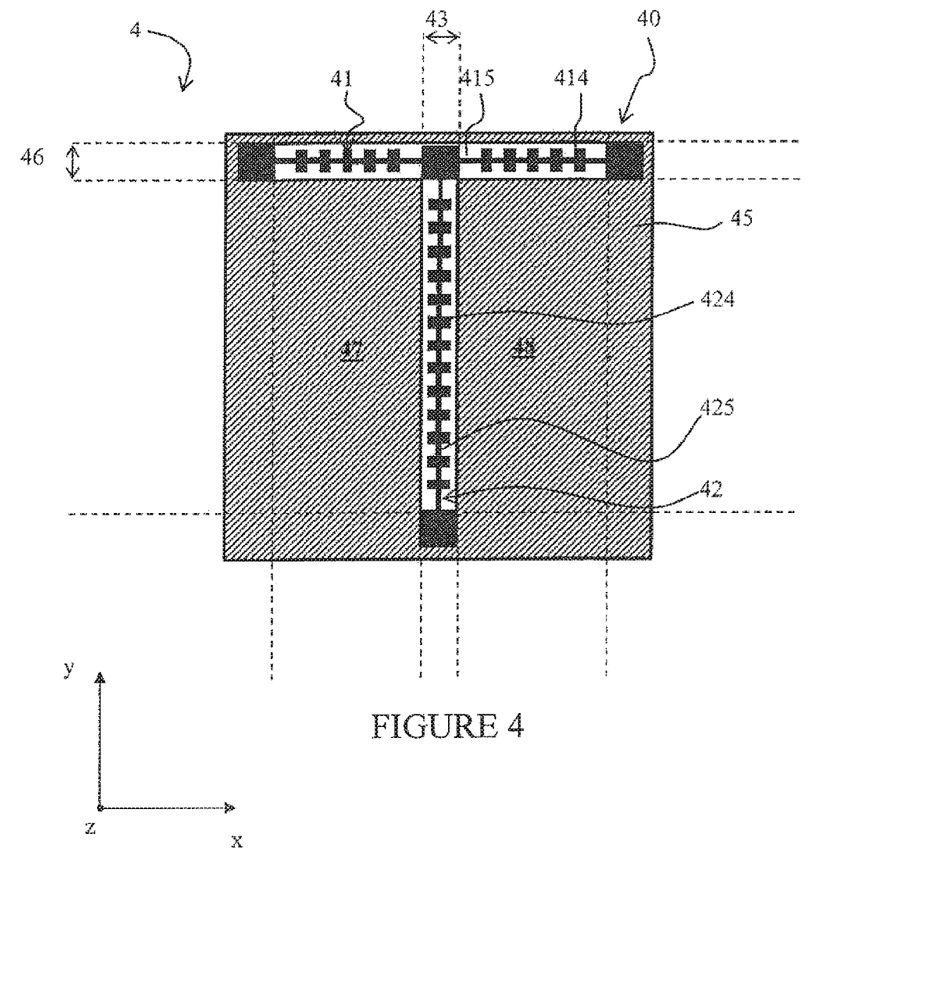
FIG. 4 is a top view of a fourth embodiment of a device according to the invention that is an alternative of the device illustrated in FIG. 3.

Reference is now made to FIG. 4, which illustrates an alternative of FIG. 3. The device 4 here again is square. It extends along the plane xy and has a thickness along the axis z perpendicular to the plane xy.

In this embodiment, the device 4 includes a flexure limiting element 40, made up of two elements 41 and 42. It is arranged inside the device 4.

These two elements 41 and 42 extend in two different directions, here two perpendicular directions.

One of the elements 41 extends along one of the sides of the device 4, while the other element 42 extends through the device 4, substantially in a central position.

Thus, the central element 42 makes it possible to define two zones 47 and 48 of the total surface of the device. Each of the zones is in the extension of the lateral element 41 along the axis y.

The device includes flexure-sensitive elements over its entire surface, with the exception of the zones 43 and 46 occupied by the element 40.

Each of these elements 41, 42 includes a central part 415, 425, on either side of which protruding parts 414, 424 extend. The central part 415 extends along the plane xz and the central part 425 extends along the plane yz.

In the configuration illustrated in FIG. 4, the flexure limiting element 40 makes it possible to protect the flexure-sensitive elements by limiting the flexure of the device 4 at the whole surface of the device 4 relative to any axis parallel to the axis x or to the axis y.

The element 40 makes it possible, owing to the element 41, to limit the flexure of the device 4 to a determined curve radius at the zones 47 and 48 relative to an axis parallel to the axis y. The element 40 also makes it possible to limit the flexure of the device 40 to a determined curve radius at the zones 47 and 48 relative to an axis parallel to the axis x, owing to the element 42. To that end, it suffices for the height H and the spacing L of the protruding parts to be such that L<πH, and preferably, L<2H.

The element 40 completely prevents the flexure at the zone 43 along an axis parallel to the axis y, as well as the flexure at the zone 46 relative to any axis parallel to the axis x. However, the element 40 may conform to part of the human body.

Indeed, the surface occupied by the element 40 will still be less than 50% of the total surface of the device 4, preferably less than 10%.

Figure 5:
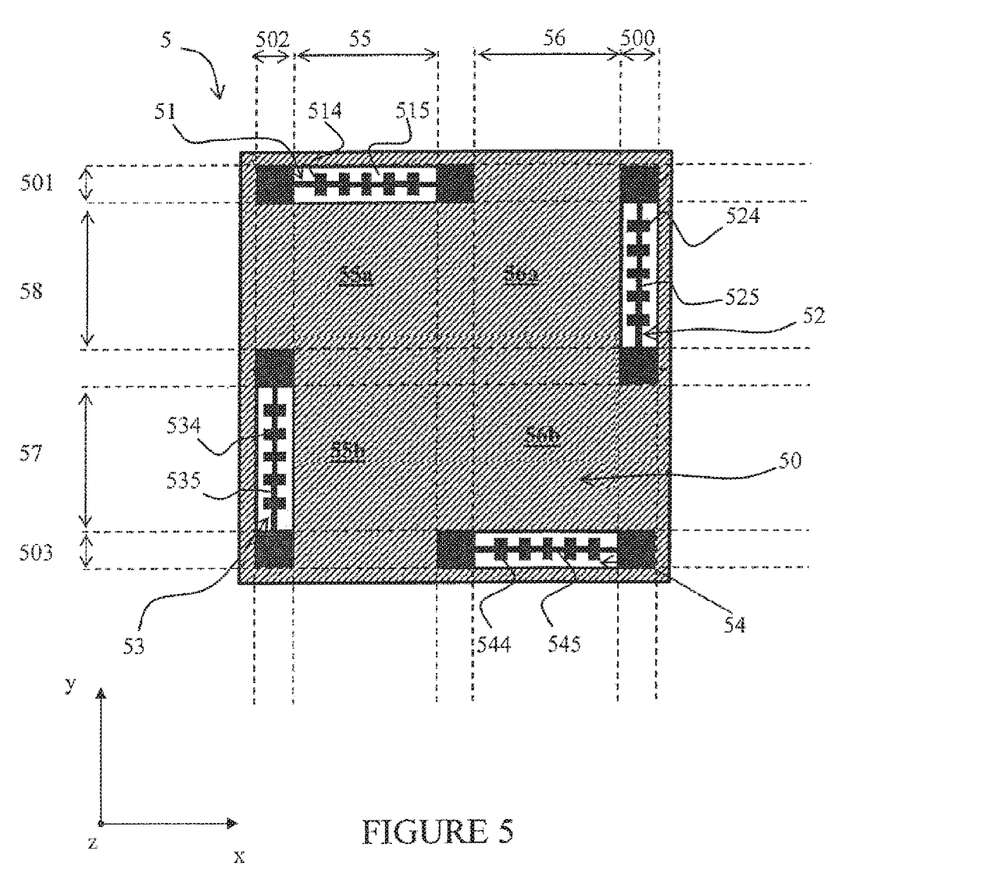
FIG. 5 is a top view of a fifth embodiment of the device according to the invention.

Reference is now made to FIG. 5, which illustrates another embodiment of the device according to the invention.

The device 5 here again has a shape that is preferably square and substantially planar. It defines a surface 50 including flexure-sensitive components that extend in the plane xy. The device also has a thickness along the axis z perpendicular to the plane xy.

In the device 5, several flexion limiting elements are provided, here four.

The elements 51, 52, 53 and 54 here have the same general structure, i.e., an elongated central part 515, 525, 535 and 545, on either side of which protruding parts 514, 524, 534 and 544 extend.

Each of these elements 51 to 54 is arranged parallel to a side of the device 5, such that its central part is substantially parallel to the side.

Furthermore, in the example illustrated in FIG. 5, each of the elements 51 to 54 has a length smaller than that of a side of the device, such that spaces are arranged between each of them.

These flexure limiting elements 51, 52, 53 and 54 define several zones in the surface 50: zones 55 and 56 in the extension of the elements 51 and 54 along the axis y and zones 57 and 58 in the extension of the elements 52 and 53 along the axis x.

In practice, these zones have shared parts. Thus, the zone 55 comprises the zones 55a and 55b, the zone 55a being shared with the zone 58 and the zone 55b being shared with the zone 57. Likewise, the zone 56 comprises the zones 56a and 56b, the zone 56a being shared with the zone 58 and the zone 56b being shared with the zone 57.

Furthermore, the zones 500, 501, 502 and 503 correspond to a side of the surface partially occupied by one of the elements 51 to 54.

The presence of the elements 51 to 54 makes it possible to protect the flexure-sensitive elements by limiting the flexure of the device 5 at the whole surface 50 of the device, along any axis parallel to the axis x or the axis y.

The flexure limiting element 51 makes it possible to limit the flexure of the device 5 to a determined curve radius at the zone 55 relative to an axis parallel to the axis y.

The element 51 will completely prevent the flexure at the zone 501 relative to any axis parallel to the axis x.

The flexure limiting element 54 makes it possible to limit the flexure of the device 5 to a determined curve radius at the zone 56 along any axis parallel to the axis y.

The element 54 completely prevents the flexure at the zone 503 relative to any axis parallel to the axis x.

The flexure limiting element 53 makes it possible to limit the flexure of the device 5 to a determined curve radius at the zone 57 relative to any axis parallel to the axis x.

The element 53 completely prevents the flexure at the zone 52 along any axis parallel to the axis y.

The flexure limiting element 52 makes it possible to limit the flexure of the device 50 to a determined curve radius at the zone 58 along any axis parallel to the axis x. The element 52 completely prevents the flexure at the zone 500 along any axis parallel to the axis y.

Figure 6:
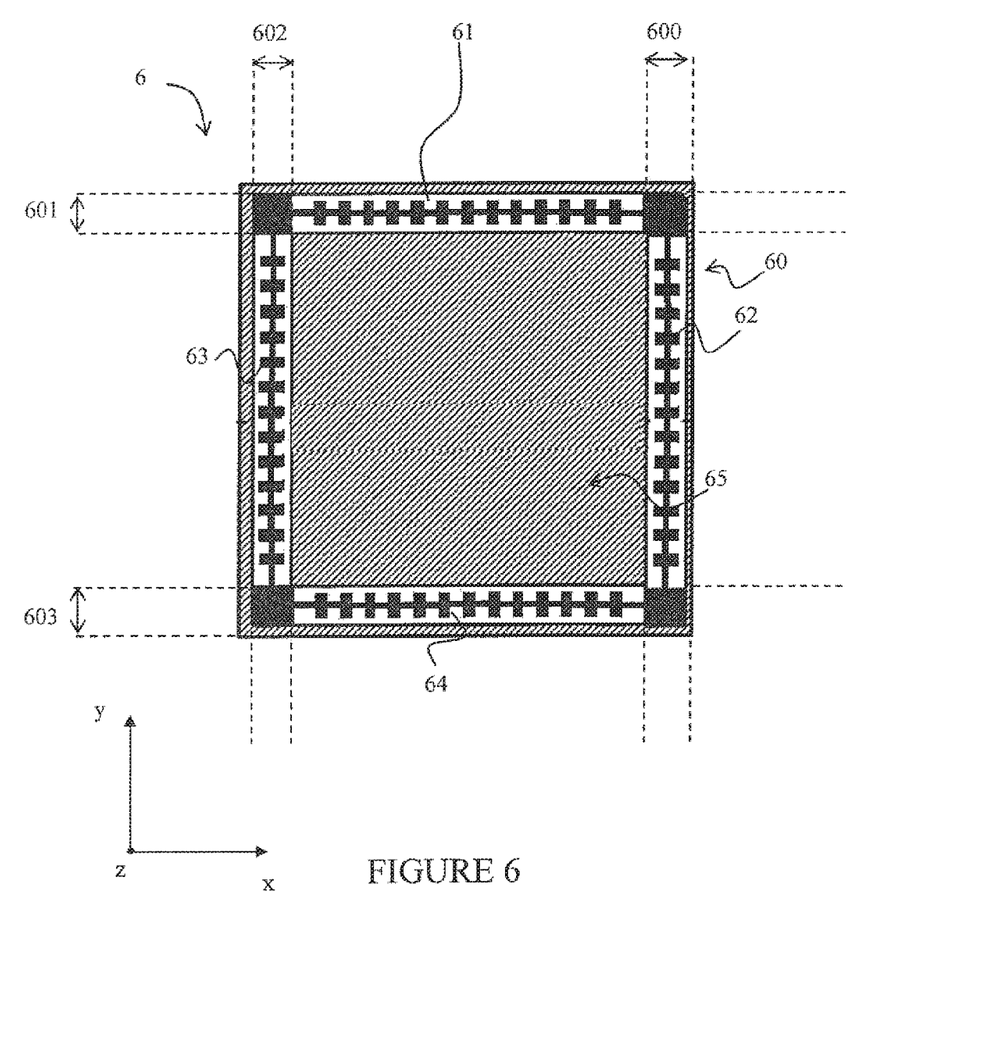
FIG. 6 is a top view of a sixth embodiment of the device according to the invention, which is an alternative of the device illustrated in FIG. 5.

Reference is now made to FIG. 6, which illustrates an alternative embodiment of the device illustrated in FIG. 5.

The device 6 here again has a substantially square and planar shape. In the plane xy, it defines a surface 65.

According to this alternative, the device 6 includes a flexure limiting element 60 that is made up of four parts 61, 62, 63 and 64. Each of these parts is arranged along one of the sides of the device and has a length slightly smaller than that of each side. Thus, the element 60 in practice constitutes a single element made up of orthogonal parts in pairs and arranged at the periphery of the device 6.

The general structure of the elements 61 to 64 will not be described in detail, since it is similar to that of the devices 51 to 54.

The element 60 makes it possible to limit the flexure to a determined curve radius of the entire surface 65 of the device not occupied by the elements 61 to 64, whether the flexure occurs along the axis x or the axis y.

Furthermore, each of the elements 61 and 64 completely prevents the flexure at the zones 601 and 603, corresponding to the parts of the surface occupied by these elements 61 and 64, relative to any axis parallel to the axis x and each of the elements 62, 63 completely prevents the flexure at the zones 600 and 602 occupied by these elements relative to any axis parallel to the axis y.

The invention is not limited to the general structure of a flexure limiting element as described in reference to FIGS. 1 to 6. Other elements making it possible to limit the flexure may be used. Indeed, it is possible to consider modifying the distribution, shape and dimensions of the protruding parts and the recesses of these elements.

In particular, another flexure limiting element may include a central part and protruding parts, the central part having different orientations.

Figure 11A:
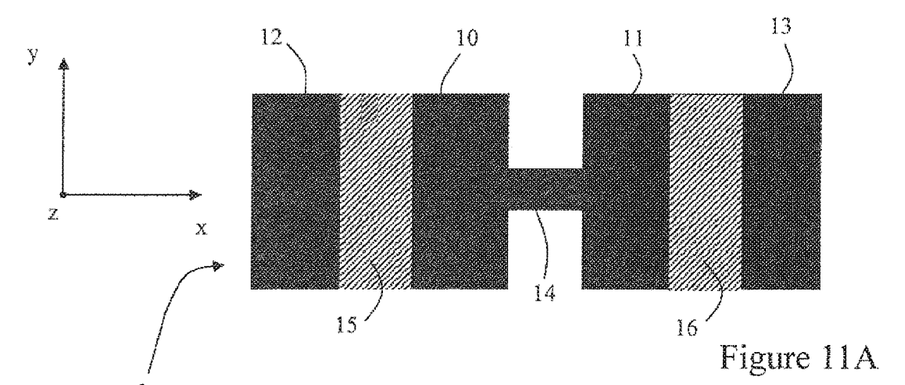
Figure 11B:
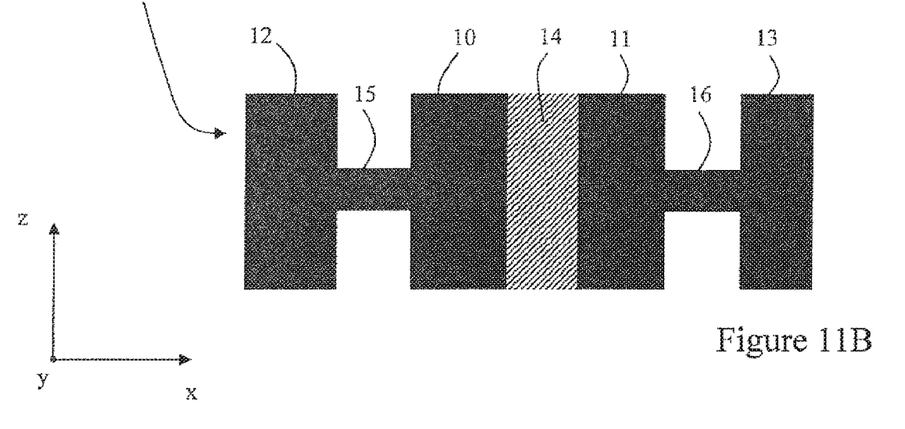

This alternative embodiment is illustrated in FIGS. 11A and 11B.

FIG. 11A is a top view (or in plane xy) of a flexure limiting element 1. It includes four protruding tabs 10 to 13 connected in pairs by a central part 14 to 16, these central parts not all having the same orientation.

Thus, the central parts 15 and 16 extend in the plane xy, while the central part 14 extends along the plane xz perpendicular to the plane xy.

FIG. 11B illustrates this same element 1, seen from the side (or in the plane xz).

Furthermore, the flexure limiting elements can be designed to limit the flexure to curve radii different from one another.

Lastly, in all of the example embodiments, the device may consist of a substrate or a unit, both including flexure-sensitive elements.

Furthermore, the invention is not limited to the specific locations of the flexure limiting elements that have been described in reference to these figures. These elements could be arranged differently and still perform their function, inasmuch as the flexure axis does not pass through the central part of the elements.

In the preceding description, the device according to the invention has a planar and square shape. However, the invention is not limited to this embodiment, and the device could assume other forms.

Thus, the device may for example be rectangular, triangular or disc-shaped. The choice of the shape of the device may depend on various criteria, such as the morphology of the person or the zone of the human body to be electrically stimulated.

Figure 7:
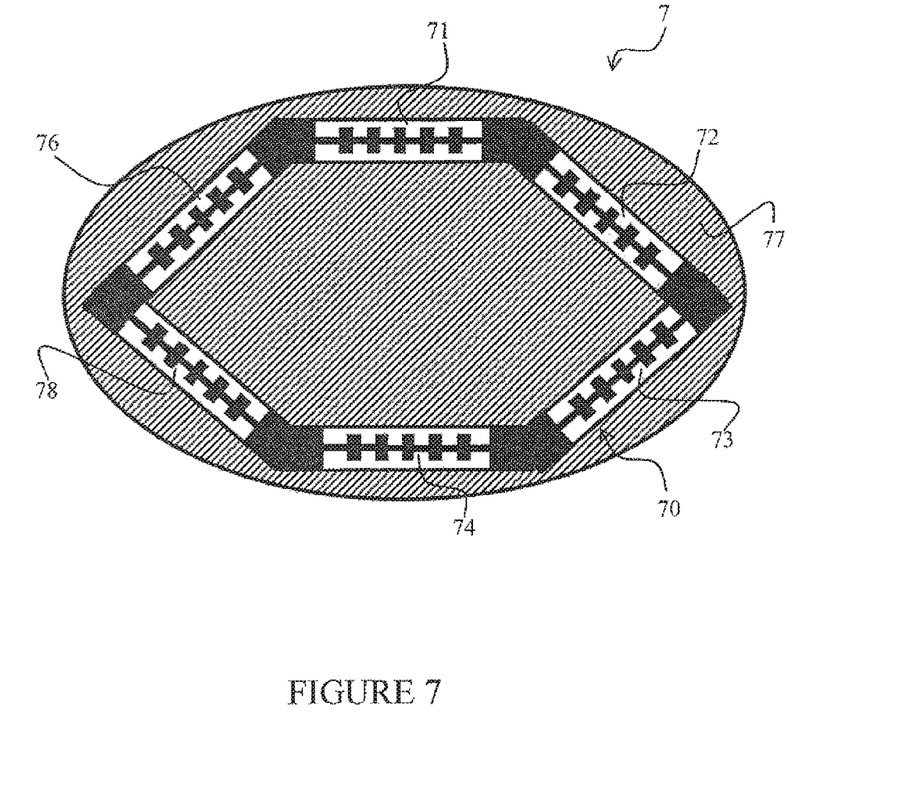
FIG. 7 is a top view of a seventh embodiment of the device according to the invention, FIG. 8 comprises FIGS. 8A, 8B, and 8C, FIG. 8A being a top view of part of an eighth embodiment of the device according to the invention, FIG. 8B being a sectional view along an axis parallel to the axis VIII-VIII of FIG. 8A, and FIG. 8C being a sectional view along the same axis of the whole device, FIG. 9 comprises FIGS. 9A and 9B corresponding to a top view and a sectional view along line A-A of a ninth embodiment of the device according to the invention, FIG. 10 comprises FIGS. 10A and 10B, which show, in top view and in sectional view along axis X-X, a tenth embodiment of the device according to the invention, and FIG. 11 comprises FIGS. 11A and 11B, which show top and side views of an alternative embodiment of a flexure limiting element as illustrated in FIG. 3.

An example of an oval the base is illustrated in FIG. 7.

On the surface 77 of the device 7, flexure-sensitive components are provided.

Furthermore, a flexure limiting element 70 making it possible to limit the flexure is provided in the device 7.

This flexure limiting element 70 here is made up of six parts 71 to 76. The six parts are, in practice, connected to one another so as to form only one element.

The six parts thus form a hexagon. Each of them has a configuration similar to that for example of the part 51 illustrated in FIG. 5 and will not be described in detail again.

The number and length of the different parts could be modified so that the flexure limiting element is arranged closer to the periphery of the surface 77, so as to increase the available space able to accommodate flexure-sensitive elements.

Figures 8A, 8B, 8C:
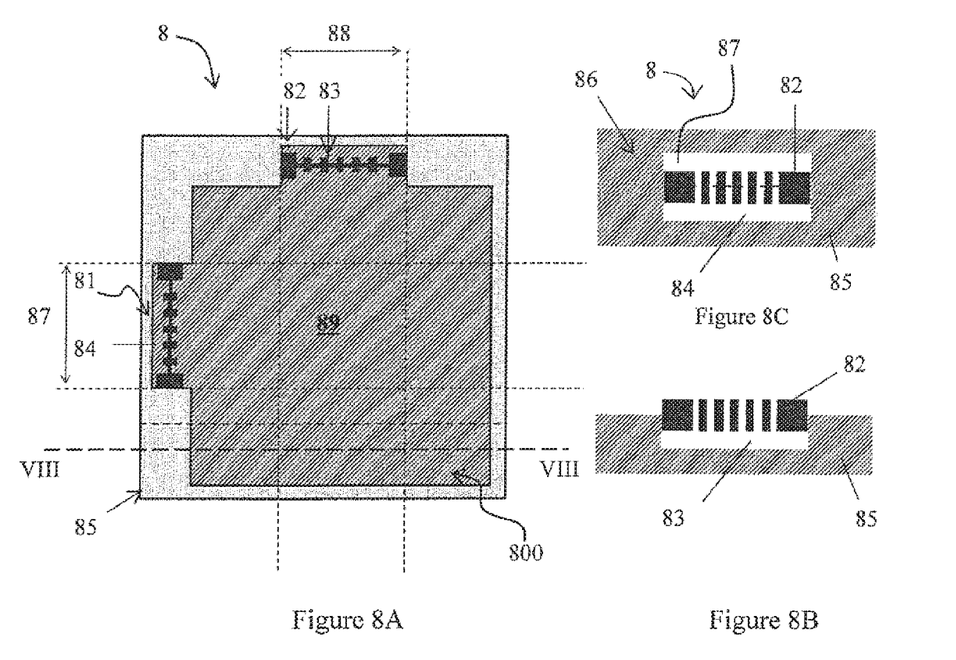

Reference is now made to FIG. 8, which illustrates an alternative in which the flexure limiting elements are integrated inside the packaging (or encapsulating unit) in which the elements necessary to produce a cutaneous device according to the invention are housed (batteries, electronic components, metal tracks, etc.).

As will be seen in light of FIG. 8, this configuration has the advantage that these flexure limiting elements are not visible to the user.

Thus, in this embodiment, the encapsulating unit 8 includes two parts 85 and 86.

Reference is first made to FIG. 8A, which is a top view of the first part 85.

Thus, two cavities 83 and 84 are present within the unit 8, in which elements 81 and 82 making up the flexure limiting device can be inserted.

FIG. 8B is a sectional view along an axis parallel to the axis VIII-VIII and passing through the cavity 83.

This FIG. 8B illustrates an element 82 limiting the flexure within the cavity 83 arranged in the first part 85 of the unit.

FIG. 8C is a sectional view along the same axis as FIG. 8B of the packaging, made up of two parts 85 and 86.

FIG. 8C shows that the second part 86 also includes a cavity 87 able to accommodate the flexure limiting element 82.

Furthermore, inside the unit 8, a cavity is also defined in which a substantially planar device 800 is arranged that includes flexure-sensitive elements.

In order to decrease the thickness of the unit 8, the element(s) making it possible to limit the flexure can be in contact with the walls of the two parts 85 and 86 of the unit, the cavities then being dimensioned to receive an element, without a free space remaining.

The element 81 makes it possible to define a zone 87 of the device 800, in its extension along the axis x, and the element 82 makes it possible to define a zone 88, in its extension along the axis y.

Thus, the element 81 will make it possible to limit the flexure at the zone 87 relative to any axis parallel to the axis x and the element 82 will make it possible to limit the flexure at the zone 88 relative to any axis parallel to the axis y. In practice, in the zone 89 corresponding to the intersection of the two zones 87 and 88, the components are protected from the effects of flexure relative to an axis parallel to the axis x or the axis y.

Figure 9A:
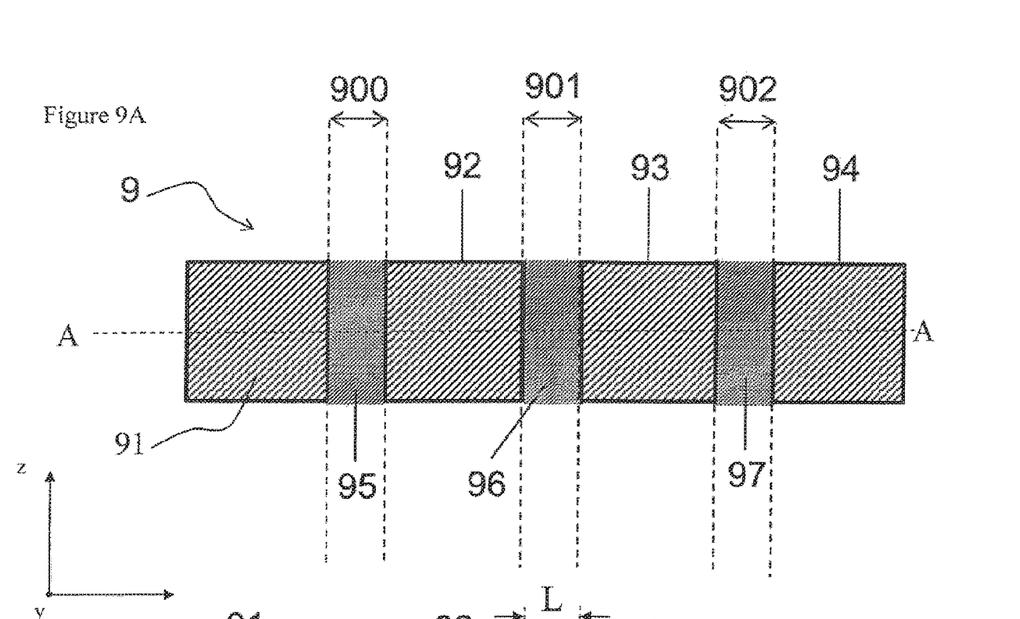
Figure 9B:
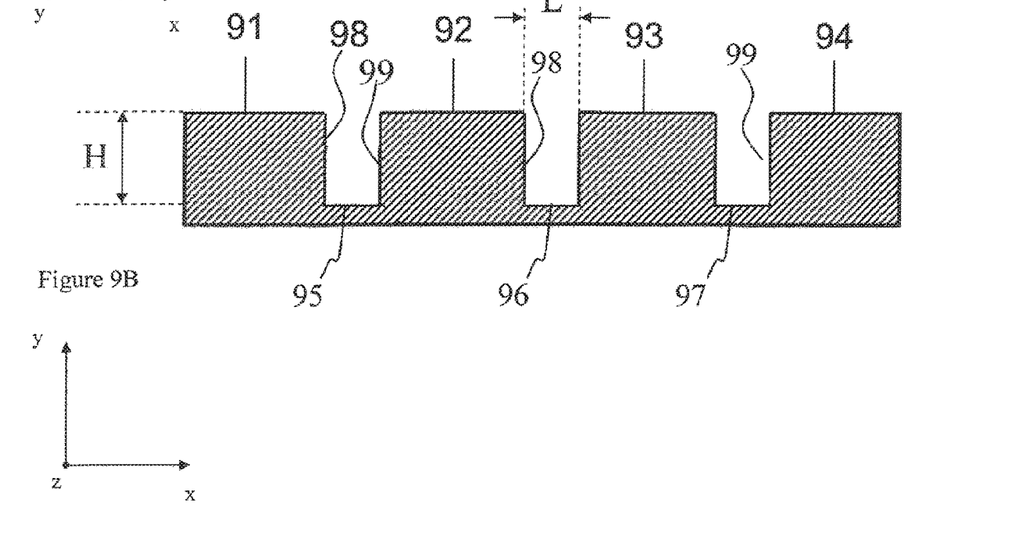
Figure 10A:
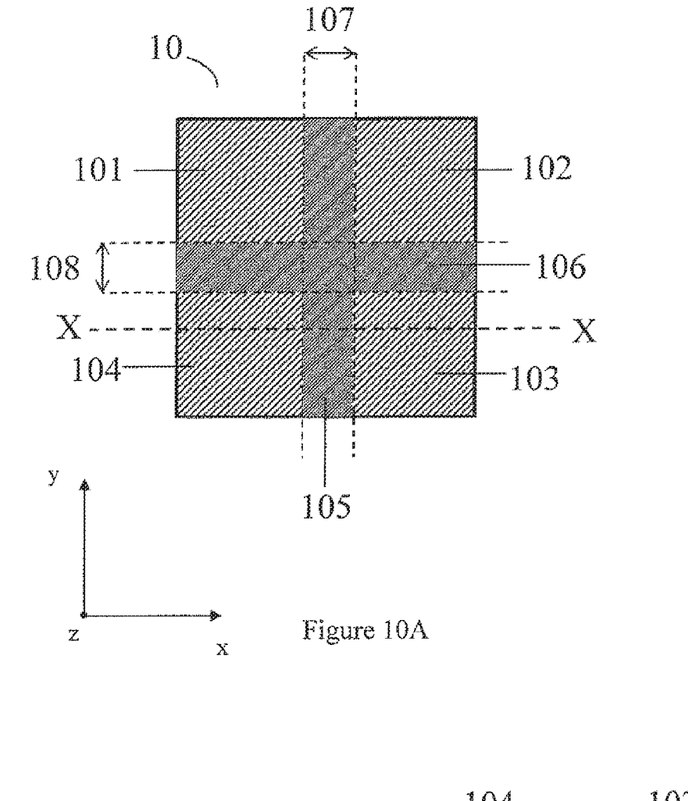
Figure 10B:
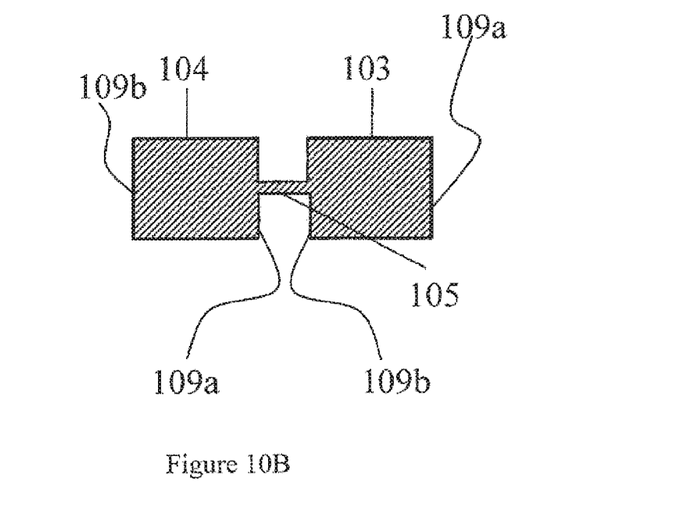

Reference is now made to FIGS. 9 and 10, which describe embodiments in which the encapsulating unit of the device according to the invention contributes to the limitation of the flexure within the device.

Reference is first made to FIGS. 9A and 9B, which show, in top view and in sectional view along line AA, another embodiment of the device according to the invention.

Thus, the device 9 is made up of four rigid parts 91, 92, 93 and 94 that are connected to one another by flexible parts 95, 96 and 97. All of these parts are inside the encapsulating unit. These flexible parts ensure the flexibility of the device 9 relative to any axis parallel to the axis y, at the zones 900, 901 and 902. Metal tracks making it possible to electrically connect the four rigid parts are present at the flexible zones and make up flexure-sensitive elements.

In the example illustrated in FIG. 9, owing to the shape of the encapsulating unit, each of the rigid parts 91 to 94 has a substantially square cross-section (in the plane xy), and each of the flexible parts 95 to 97 is in the form of a strip.

Thus, the encapsulating unit defines, at each rigid part, a wall 98 across from a wall 99, these two walls 98 and 99 being substantially perpendicular to the flexible part connecting two adjacent rigid parts.

Owing to this configuration, when flexure occurs relative to an axis parallel to the axis y within a zone 900, 901 or 902, and this flexure tends to bring the walls 98 and 99 closer to one another (upward flexure), the latter will come into contact with one another in the zone opposite the corresponding flexible part, and as a result, limit the flexure of the device 9 relative to this axis. To that end, it suffices for the height H of the walls 98 and 99 and the spacing L between the walls to be such that $L < \pi H$, and preferably $L < 2H$.

It will be understood that this configuration has the advantage of not requiring the introduction of specific elements within the flexure limiting device, this function being performed by the encapsulating unit.

Reference is now made to FIG. 10, which is an alternative embodiment of the device illustrated in FIG. 9.

In this embodiment, the device 10 is made up of four rigid parts 101, 102, 103 and 104 and two flexible parts 105 and 106 that connect the rigid parts in pairs.

In the example illustrated in FIG. 10, each of the rigid parts 101 to 104 has a substantially square section and each of the flexible parts 105, 106 is in the form of a strip, the two flexible parts forming a cross. All of these parts of the device are inside an encapsulating unit.

Thus, each rigid part includes two walls of the encapsulating unit 109a and 109b that extend substantially perpendicular to the flexible parts.

The flexible parts 105 and 106 provide the flexibility of the device 10 relative to any axis parallel to the axis y in the zone 107 and relative to any axis parallel to the axis x in the zone 108.

FIG. 10B, which is a sectional view along the axis X-X, makes it possible to understand that the walls of the encapsulating unit 109a and 109b will make it possible to limit the flexure of the device 10 to a determined curve radius, when these two walls come into contact due to a flexure of the device 10 along an axis parallel to the axis y within the zone 107, whether this flexure occurs upward or downward.

The reference signs inserted after the technical features appearing in the claims are intended solely to facilitate the understanding of the latter and cannot limit its scope.

The invention claimed is:

1. A device for securing flexure-sensitive components to the skin of a user while substantially conforming to a shape of the user's skin but without damaging the flexure-sensitive components, the device, having a surface, comprising:
  an element having a thickness in which flexure-sensitive components are situated, the element being substantially planar in its original form and having at least one first flexible zone in which the device can be bent relative to an axis situated in a plane of the device and in which the flexure-sensitive components are situated;
  at least two flexure limiting elements received within the element that are configured for limiting a flexure of said at least one first flexible zone of the device relative to at least two axes situated in the plane of the device, the at least two flexure limiting elements each comprising:
    protruding parts having first and second opposing sides extending along at least a portion of the thickness of the element;
    a first central part extending from the first and second opposing sides along an axis extending along the protruding parts, and
    a second central part extending from the first and second opposing sides along an axis different from the axis of the protruding parts,
  an encapsulating unit for housing the element and the at least two flexure limiting elements, the encapsulating unit comprising:
    a first part having at least a first wall extending along a first axis; and
    a second part having at least a second wall extending along an axis different from the first axis of the first wall;
  wherein the protruding parts are connected in pairs by the first and second central parts, said first and second central parts not all having a same orientation, so that the protruding parts define recesses between them; and
  wherein the element and the at least two flexure limiting elements are received between the first and second parts, and wherein a portion of one of the at least two flexure limiting elements is in contact with the first wall and a portion of the other of the at least two flexure limiting elements is in contact with the second wall.

2. The device according to claim 1, wherein a height (H) of the protruding parts and a width (L) corresponding to a recess between the protruding parts are such that $L<\pi H$.

3. The device according to claim 1, wherein the at least two flexure limiting elements are situated in a substantially central region of the device.

4. The device according to claim 1, wherein the at least two flexure limiting elements are situated along at least part of a periphery of the device.

5. The device according to claim 4, wherein the at least two flexure limiting elements include a part situated at the periphery of the device and a part extending substantially at a center of the device.

6. The device according to claim 1, wherein a surface of said at least two flexure limiting elements is less than 50% of the surface of the device.

7. The device according to claim 1, wherein the encapsulating unit further includes at least third and fourth flexure limiting elements connected to one another by a second flexible zone and extending along a determined direction.

8. The device according to claim 7, wherein the second flexible zone extends along a direction different than a direction of the first flexible zone.

9. The device according to claim 1, wherein a height (H) of said first and second walls and a width (L) of a spacing between the first and second walls are such that $L<\pi H$.

10. A device for securing flexure-sensitive components to the skin of a user while substantially conforming to a shape of the user's skin but without damaging the flexure-sensitive components, the device, having a surface, comprising:
  an element having a thickness in which flexure-sensitive components are situated, the element being substantially planar in its original form and having at least one first flexible zone in which the device can be bent relative to at least two axes situated in a plane of the device and in which the flexure-sensitive components are situated;
  at least two flexure limiting elements received within the element that are configured to limit a flexure of said at least one first flexible zone of the device relative to at least two axes situated in the plane of the device, the at least two flexure limiting elements each comprising:
    protruding parts having first and second opposing sides extending along at least a portion of the thickness of the element;
    a first central part extending from the first and second opposing sides along an axis extending along the protruding parts,
    a second central part extending from the first and second opposing sides along an axis different from the axis of the protruding parts,
  wherein the protruding parts are connected in pairs by central parts, said central parts not all having a same orientation.

11. The device according to claim 10, wherein a height (H) of the protruding parts and a width (L) corresponding to a recess between the protruding parts are such that $L<\pi H$.

12. The device according to claim 10, wherein the at least two flexure limiting elements are situated in a substantially central region of the device.

13. The device according to claim 10, wherein the at least two flexure limiting elements are situated along at least part of a periphery of the device.

14. The device according to claim 10, wherein the at least two flexure limiting elements include a part situated at a periphery of the device and a part extending substantially at a center of the device.

15. The device according to claim 10, wherein a surface of the at least two flexure limiting elements is less than 50% of the surface of the device.

16. The device according to claim 10, wherein the at least two flexure limiting elements are received within an encapsulating unit of the device.

17. The device according to claim 16, wherein the encapsulating unit includes at least first and second parts, the first part comprising a first wall extending along a first axis and the second part comprising a second wall extending along an axis different from the first axis of the first wall, wherein one of the at least two flexure limiting elements is in contact with the first wall and wherein the other of the at least two flexure limiting elements is in contact with the second walls wall.

18. The device according to claim 17, wherein the encapsulating unit further includes at least third and fourth flexure limiting elements connected to one another by a second flexible zone and extending along a determined direction.

19. The device according to claim 18, wherein the second flexible zone extends along a direction different than a direction of the first flexible zone.

20. The device according to claim 19, wherein a height (H) of said first and second walls and a width (L) of a spacing between the first and second walls are such that $L < \pi H$.

21. The device according to claim 10, wherein the flexure-sensitive components comprise electronic components, metal tracks, printed circuits or power sources.

22. The device according to claim 2, wherein the height (H) of the protruding parts and the width (L) are such that $L < 2H$.

23. The device according to claim 6, wherein the surface of said at least two flexure limiting elements is less than 10% of the surface of the device.

24. The device according to claim 9, wherein the height (H) of said first and second walls and the width (L) of the spacing between the first and second walls are such that $L < 2H$.

25. The device according to claim 11, wherein the height (H) of the protruding parts and the width (L) corresponding to the recess between the two protruding parts are such that $L < 2H$.

26. The device according to claim 15, wherein the surface of the at least two flexure limiting elements is less than 10% of the surface of the device.

27. The device according to claim 20, wherein the height (H) of said first and second walls and the width (L) of the spacing between the first and second walls are such that $L < 2H$.

* * * * *